Figure 1:
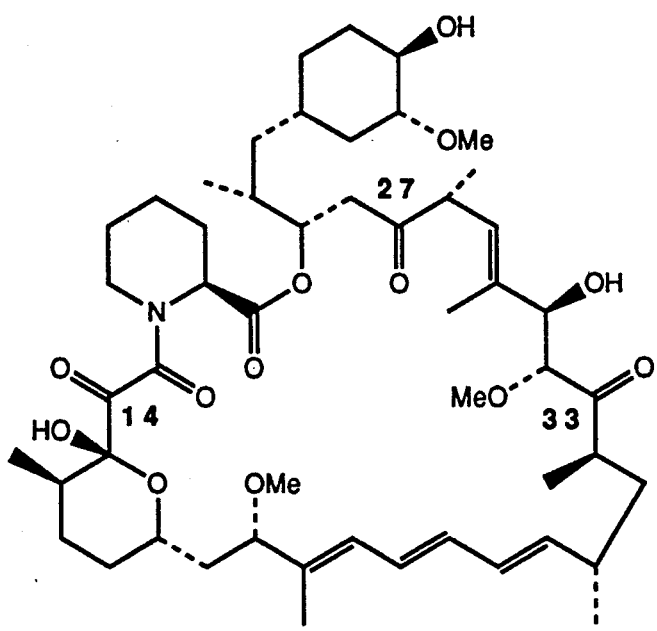

United States Patent [19]

Caufield et al.

[11] Patent Number: 5,023,264
[45] Date of Patent: Jun. 11, 1991

[54] RAPAMYCIN OXIMES

[75] Inventors: Craig E. Caufield, Plainsboro; Amedeo A. Failli, Princeton Juncton, both of N.J.

[73] Assignee: American Home Products Corporation, New York, N.Y.

[21] Appl. No.: 553,720

[22] Filed: Jul. 16, 1990

[51] Int. Cl.$^5$ .................. A61K 31/395; C07D 491/16
[52] U.S. Cl. .................................... 514/291; 540/456; 546/90
[58] Field of Search .......................... 540/456; 546/90; 514/291

[56] References Cited

U.S. PATENT DOCUMENTS

| | | | |
|---|---|---|---|
| 3,929,992 | 12/1975 | Sehgal | 424/122 |
| 3,993,749 | 11/1976 | Sehgal | 424/122 |
| 4,316,885 | 2/1982 | Rakhit | 424/122 |
| 4,401,653 | 4/1983 | Eng | 424/114 |
| 4,650,803 | 3/1987 | Stella | 514/291 |
| 4,885,171 | 12/1989 | Surendra | 424/122 |

OTHER PUBLICATIONS

J. Antibiot. 28, 721-726 (1975).
J. Antibiot. 28, 727-732 (1975).
J. Antibiot. 31, 539-545 (1978).
Can. J. Physiol. Pharmacol. 55, 48 (1977).
Faseb 3, 3411, 5256 (1989).
Lancet, 1183, (1978).
J. Am. Chem. Soc. 103, 3215 (1981).
Immunology, C. V. Moseby Co., pp. 12.8-12.11 (1989).

*Primary Examiner*—Robert T. Bond
*Attorney, Agent, or Firm*—Richard K. Jackson

[57] ABSTRACT

A derivative of rapamycin in which the 27-position has the structure

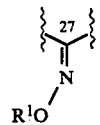

wherein
R$^1$ is hydrogen, alkyl, or —CH$_2$Ar;
Ar is

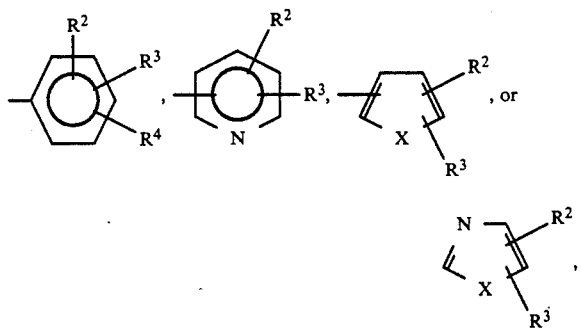

wherein R$^2$, R$^3$, and R$^4$ are each, independently, hydrogen, alkyl, aralkyl, alkoxy, hydroxy, cyano, halo, nitro, carbalkoxy, trifluoromethyl, amino, or a carboxylic acid;
X is N, O, or S;
or a pharmaceutically acceptable salt thereof, which is by virtue of its immunosuppresive activity is useful in treating transplantation rejection host vs. graft disease, autoimmune diseases, and diseases of inflammation.

9 Claims, 1 Drawing Sheet

RAPAMYCIN

RAPAMYCIN OXIMES

BACKGROUND OF THE INVENTION

This invention relates to novel oxime derivatives of rapamycin and a method for using them in the treatment of transplantation rejection, host vs. graft disease, autoimmune diseases, and diseases of inflammation.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. No. 3,922,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1976)] disclosed that rapamycin is effective in the experimental allergic encephalomyelitis model, a model for multiple sclerosis; in the adjuvant arthritis model, a model for rheumatoid arthritis; and effectively inhibited the formation of IGE-like antibodies.

The immunosuppressive effects of rapamycin have been disclosed in FASEB 3, 3411 (1989), rapamycin has been shown to be effective in inhibiting transplant rejection (U.S. patent application Ser. No. 362,544 filed Jun. 6, 1989). Cyclosporin A and FK-506, other macrocyclic molecules, also have been shown to be effective as immunosuppressive agents, therefore useful in preventing transplant rejection [FASEB 3, 3411 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides oxime derivatives of rapamycin which are useful as immunosuppressive and anti-inflammatory agents possessing the general structure of rapamycin shown in FIG. 1, where the 27 position has been transformed into an oxime having the structure

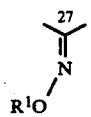

wherein
R$^1$ is hydrogen, alkyl of 1-6 carbon atoms, or —CH$_2$Ar;
Ar is

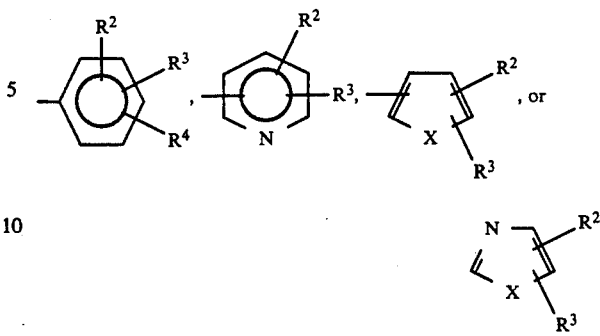

wherein R$^2$, R$^3$, and R$^4$ are each, independently, hydrogen, alkyl of 1-6 carbon atoms, aralkyl of 7-10 carbon atoms, alkoxy of 1-6 carbon atoms, hydroxy, cyano, halo, nitro, carbalkoxy of 2-7 carbon atoms, trifluoromethyl, amino, or a carboxylic acid;
X is N, O, or S;
or a pharmaceutically acceptable salt thereof.

Of the compounds, preferred members are those in which R$^1$ is hydrogen, alkyl of 1-6 carbon atoms, or

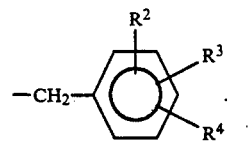

The pharmaceutically acceptable salts may be formed from inorganic cations such as sodium, potassium, and the like.

Although compounds of this invention can be prepared by conventional methods that are disclosed in the literature, because functional groups are contained in a large macrocyclic ring, functional group reactivity cannot be readily predicted [R. B. Woodward et al., J. Am. Chem. Soc. 103, 3215 (1981)]. Rapamycin has carbonyl groups at the 14- and 27- and 33-positions. Based on x-ray crystallographic analysis, the 33-position was predicted to be the most reactive center; unexpectedly however, oxime formation occurred exclusively at the 27-position.

The compounds of the invention can be prepared by the following route from rapamycin.

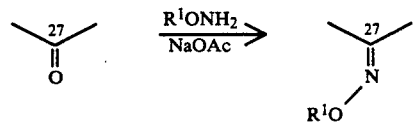

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio:

$$\frac{^3H\text{-control thymus cells} - H^3\text{-rapamycin-treated thymus cells}}{^3H\text{-control thymus cells} - H^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3H\text{-PLN cells control C3H mouse} -}{^3H\text{-PLN cells rapamycin-treated C3H mouse}}$$
$$\frac{^3H\text{-PLN cells control C3H mouse} -}{^3H\text{-PLN cells test compound-treated C3H mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385–(402), 1951. Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of representative compounds of this invention in these three standard test procedures.

TABLE 1

| Compound | LAF* (ratio) | PLN* (ratio) | Skin Graft (days + SD) |
|---|---|---|---|
| Example 1 | 0.25 | −1.40 | 10.0 ± 1.6 |
| Example 2 | 0.87 | 1.39 | 9.3 ± 1.4 |
| Example 3 | 0.007 | + | 9.5 ± 1.4 |
| Rapamycin | 1.0 | 1.0 | 12.0 ± 1.7 |

*Calculation of ratios was described supra.
+ Not evaluated

The results of these standard pharmacological test procedures demonstrate immunosuppressive activity both in vitro and in vivo for the compounds of this invention. Positive ratios in the LAF and PLN test procedures indicate suppression of T cell proliferation. Transplanted pinch skin grafts are typically rejected within 6–7 days without the use of an immunosuppressive agent. The increased survival time of the skin graft when treated with the compounds of this invention further demonstrates their utility as immunosuppressive agents. While it appears that the compound disclosed by Example 1 may cause T cell proliferation in the PLN test procedure, it is believed a negative ratio in this test procedure coupled with an increased survival time observed in the skin graft test procedure indicates a proliferation of $T_{suppressor}$ cells, which are implicated in suppressing the immune response. (see, I. Roitt et al. Immunology, C. V. Moseby Co. 1989, p 12.8–12.11).

Antifungal activity of the compounds of this invention was measured against 5 strains of *Candida albicans* using a plate test procedure for measurement of inhibition. The following represents the typical procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC (μg/ml) to inhibit growth. Surprisingly, the oxime derivatives of this invention have substantially less antifungal activity than the parent compound, rapamycin.

TABLE 2*

| | Strain of *Candida albicans* | | | | |
|---|---|---|---|---|---|
| Compound | ATCC 10231 | ATCC 38246 | ATCC 38247 | ATCC 38248 | 3669 |
| Example 1 | 0.05 | 0.2 | 0.05 | 0.1 | 0.2 |
| Example 2 | >0.4 | >0.4 | >0.4 | >0.4 | >0.4 |
| Example 3 | 0.2 | 0.05 | 0.2 | 0.05 | 0.2 |
| Rapamycin | 0.003 | 0.025 | 0.003 | 0.006 | 0.025 |

*expressed as MIC (μg/ml)

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, and inflammatory bowel disease.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sun-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

The following examples illustrate the preparation of representative compounds of this invention.

EXAMPLE 1

Rapamycin-27-oxime

To a solution of 50 mg (54.7 μmol) of rapamycin in 1 mL of methanol was added at room temperature, 12 mg (143 μmol) of anhydrous sodium acetate and 10 mg (143 μmol) of hydroxylamine hydrochloride. After 2 h stirring at room temperature, the reaction was complete by TLC. The reaction was diluted with water and extracted three times with ethyl acetate. The combined organics were washed with brine and dried over anhydrous sodium sulfate, decanted, and concentrated in vacuo to give a white, foamy solid. $^1$H NMR indicated a mixture of E and Z isomers. The solid was dissolved in hot ethyl acetate and upon cooling, white crystals formed. Vacuum filtration gave 23 mg (45%) of isomerically pure mono-oxime, which was biologically inactive (results not presented).

$^1$H NMR (CDCl$_3$, 400 MHz) δ 8.015 (s, 1H, NOH), 4.820 (s, 1H, COH), 3.414 (s, 3H, CH$_3$O—), 3.308 (s, 3H, CH$_3$O—), 1.667 (s, 3H, CH$_3$C=C), 1.652 (s, 3H, CH$_3$C=C); $^{13}$C NMR (CDCl$_3$, 100 MHz) 214.09 (C=O), 192.03 (C=O), 169.38 (C=O), 167.21 (C=O), 158.74 (C=NOH); IR (KBr) 3450 (OH), 2960 (CH), 2890 (CH), 1760 (C=O), 1740 (C=O), 1732 (C=O), 1660 (C=O, C=NOH), 1465, 1390, 1205, 1100, 1005 cm$^{-1}$; MS (neg. ion FAB) 928 (M—), 896, 590, 546, 167 (100); High Res. MS (neg. ion FAB) Calc. for C$_{51}$H$_{80}$N$_2$O$_{13}$ 928.5660, Found 928,5677.

Analysis Calcd for C$_{51}$H$_{80}$N$_2$O$_{13}$·2 H$_2$O: C63.42; H 8.21; N 2.74. Found: C63.47; H 8.11; N 2.60.

The filtrate obtained following the crystallization described above was concentrated to give a white foamy solid. The solid was dissolved in hot ethyl acetate and hexane was added until slightly cloudy. Upon cooling, white crystals formed. Vacuum filtration gave 13 mg (25%) of pure mono oxime which was a geometric isomer of the compound isolated in the previous example. This isomer was tested and found to be active in the assays described supra.

$^1$H NMR (CDCl$_3$, 400 MHz) δ 7.620 (s, 1H, NOH), 5.028 (s, 1H, COH), 3.409 (s, 3H, CH$_3$O—), 3.306 (s, 3H, CH$_3$O—), 3.172 (s, 3H, CH$_3$O—), 1.807 (s, 3H, CH$_3$C=C), 1.660 (s, 3H, CH$_3$C=C); $^{13}$C NMR (CDCl$_3$, 75 MHz) 211.83 (C=O), 191.43 (C=O), 168.73 (C=O), 167.11 (C=O), 159.94 (C=NOH); IR (KBr) 3450 (OH), 2960 (CH), 2920 (CH), 1775 (C=O), 1745 (C=O), 1680, 1650 (C=O, C=NOH), 1475, 1400, 1220, 1120, 1015 cm$^{-1}$; MS (neg. ion FAB) 928 (M—), 167 (100). High Res. MS (neg ion FAB) Calc. for C$_{51}$H$_{80}$N$_2$O$_{13}$ 928.5660, Found 928.5660.

Analysis Calcd for C$_{51}$H$_{80}$N$_2$O$_{13}$: C 65.93; H 8.68; N 3.01. Found: C 66.19; H 8.93; N 2.88.

EXAMPLE 2

Rapamycin-O-benzyl-27-oxime

To a solution of 50 mg (54.7 μmol) of rapamycin in 1 mL of methanol was added 12 mg (143 μmol) of anhydrous sodium acetate and 23 mg (143 μmol) of benzyloxyamine hydrochloride at room temperature. After 72 h stirring at room temperature, the reaction was diluted with water and extracted three times with ethyl acetate. The combined organics were washed with brine, dried over anhydrous sodium sulfate, decanted, and concentrated in vacuo to give a colorless oil. $^1$H NMR indicated a mixture of E and Z isomers. The oil was dissolved in hot diisopropyl ether/hexane and upon cooling, white crystals formed. Vacuum filtration gave 25 mg (45%) of pure mono-oxime.

$^1$H NMR (CDCl$_3$, 400 MHz) 5.031 (s, 2H, CH$_2$Ph), 3.365 (s, 3H, CH$_3$O—), 3.273 (s, 3H, CH$_3$O—), 3.118 (s, 3H, CH$_3$O—), 1.661 (s, 3H, CH$_3$C=C), 1.544 (s, 3H, CH$_3$C=C); $^{13}$C NMR (CDCl$_3$, 100 MHz) 211.65 (C=O), 191.76 (C=O), 168.78 (C=O), 166.94 (C=O), 158.46 (C=NOH); IR (KBr) 3450 (OH), 2940 (CH), 2890 (CH), 1750 (C=O), 1730 (C=O), 1650, 1630 (C=O, C=NOR), 1460, 1380, 1195, 1090, 990 cm$^{-1}$; MS (neg. ion FAB) 1018 (M—), 590, 546, 167 (100); High Res. MS (neg. ion FAB) Calc. for C$_{58}$H$_{86}$N$_2$O$_{13}$ 1018.6130, Found 1018.6157.

Analysis Calcd for $C_{58}H_{86}N_2O_{13} \cdot H_2O$: C 67.18; H 8.49; N 2.70. Found: C 67.17; H 8.61; N 2.56.

EXAMPLE 3

Rapamycin-O-methyl-27-oxime

To a solution of 750 mg (820 μmol) of rapamycin in 15 mL of methanol was added 180 mg (2.15 mmol) of anhydrous sodium acetate and 180 mg (2.15 mmol) of methoxyamine hydrochloride at room temperature. After stirring overnight at room temperature, the reaction mixture was diluted with water and extracted three times with ethyl acetate. The combined organics were washed with brine, dried over anhydrous sodium sulfate, decanted and concentrated in vacuo to give a viscous oil. $^1$H NMR indicated a mixture of E and Z isomers. The solid was dissolved in hot diisopropyl ether/hexane and upon cooling, white crystals formed. Vacuum filtration gave 370 mg (48%) of pure mono-oxime.

$^1$H NMR (CDCl$_3$, 400 MHz) δ 4.960 (bs, 1H, COH), 3.794 (s, 3H, CH$_3$ON=C), 3.395 (s, 3H, CH$_3$O—), 3.288 (s, 3H, CH$_3$O—), 3.121 (s, 3H, CH$_3$O—), 1.645 (s, 3H, CH$_3$C=C), 1.587 (s, 3H, CH$_3$C=C); $^{13}$C NMR (CDCl$_3$, 100 MHz) 211.70 (C=O), 192.11 (C=O), 168.75 (C=O), 166.84 (C=O), 158.08 (C=NOMe); IR (KBr) 3450 (OH), 2940 (CH), 2890 (CH), 1750 (C=O), 1655, 1635 (C=O, C=NOCH$_3$), 1455, 1380, 1195, 1090, 1050, 990 cm$^{-1}$; MS (neg. ion FAB) 942 (M—), 590, 546, 167 (100); High Res. MS (neg. ion FAB) Calc. for $C_{52}H_{82}N_2O_{13}$, 942.5818, Found 942.5863.

Analysis Calcd for $C_{52}H_{82}N_2O_{13} \cdot H_2O$: C 65.00; H 8.75; N 2.91. Found: C 65.20; H 8.83; N 2.50.

What is claimed is:

1. A derivative of rapamycin in which the 27-position has the structure

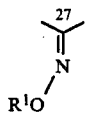

wherein
R$^1$ is hydrogen, alkyl of 1–6 carbon atoms, or —CH$_2$Ar;
Ar is

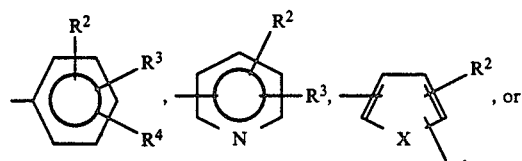

wherein R$^2$, R$^3$, and R$^4$ are each, independently, hydrogen, alkyl of 1–6 carbon atoms, aralkyl of 7–10 carbon atoms, alkoxy of 1–6 carbon atoms, hydroxy, cyano, halo, nitro, carbalkoxy of 2–7 carbon atoms, trifluoromethyl, amino, or a carboxylic acid;

X is N, O, or S;
or a pharmaceutically acceptable salt thereof.

2. A compound of claim 1 wherein R$^1$ is alkyl of 1–6 carbon atoms or a pharmaceutically acceptable salt thereof.

3. A compound of claim 1 wherein R$^1$ is

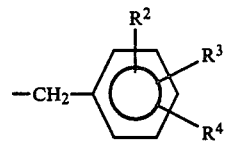

or a pharmaceutically acceptable salt thereof.

4. A compound of claim 1 which is rapamycin-27-oxime or a pharmaceutically acceptable salt thereof.

5. A compound of claim 1 which is rapamycin-O-benzyl-27-oxime or a pharmaceutically acceptable salt thereof.

6. A compound of claim 1 which is rapamycin-O-methyl-27-oxime or a pharmaceutically acceptable salt thereof.

7. A method of treating transplantation rejection, host vs. graft disease, autoimmune diseases, and diseases of inflammation in a mammal by administering an effective amount of a compound which is a derivative of rapamycin in which the 27-position has the structure;

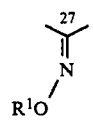

wherein
R$^1$ is hydrogen, alkyl of 1–6 carbon atoms, or —CH$_2$Ar;
Ar is

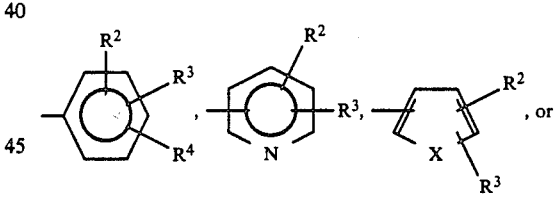

wherein R$^2$, R$^3$, and R$^4$ are each, independently, hydrogen, alkyl of 1–6 carbon atoms, aralkyl of 7–10 carbon atoms, alkoxy of 1–6 carbon atoms, hydroxy, cyano, halo, nitro, carbalkoxy of 2–7 carbon atoms, trifluoromethyl, amino, or a carboxylic acid;
X is N, O, or S;
or a pharmaceutically acceptable salt thereof.

8. A pharmaceutical composition comprising a compound of claim 1 or a pharmaceutically acceptable salt thereof and a pharmaceutically acceptable carrier.

9. A composition as claimed in claim 8, in unit dosage form.

* * * * *